(12) United States Patent
Pfister

(10) Patent No.: US 7,156,554 B2
(45) Date of Patent: Jan. 2, 2007

(54) METHOD OF COMPENSATING FOR IMAGE FAULTS IN AN X-RAY IMAGE RECORDING

(75) Inventor: Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/144,998

(22) Filed: Jun. 3, 2005

(65) Prior Publication Data

US 2005/0281376 A1 Dec. 22, 2005

(30) Foreign Application Priority Data

Jun. 3, 2004 (DE) .................... 10 2004 027 163

(51) Int. Cl.
*G21K 1/02* (2006.01)
(52) U.S. Cl. .................. 378/207; 378/62; 378/154; 378/205
(58) Field of Classification Search .................. 378/62, 378/147, 149, 154, 155, 205, 207
See application file for complete search history.

(56) References Cited

U.S. PATENT DOCUMENTS

| 5,241,578 | A | * | 8/1993 | MacMahon | 378/154 |
| 5,388,143 | A | * | 2/1995 | MacMahon | 378/206 |
| 6,422,750 | B1 | * | 7/2002 | Kwasnick et al. | 378/205 |
| 6,702,459 | B1 | * | 3/2004 | Barnes et al. | 378/197 |
| 7,070,328 | B1 | * | 7/2006 | Geiger et al. | 378/207 |

* cited by examiner

*Primary Examiner*—Allen C. Ho

(57) ABSTRACT

Method for compensating for image faults in a digital image recording which has been created by an x-ray system consisting of a radiographic source, an anti-scatter grid and a digital x-ray detector such as an image amplifier or a solid-state image detector, said image faults resulting from decentering, defocusing or defects in the anti-scatter grid or by the Heel effect and causing an intensity reduction of the primary radiation falling on the x-ray detector, characterized in that the actual reduction in intensity is measured through the anti-scatter grid and correction parameters are determined based on the measured values recorded which are then used to correct the x-ray image recording.

15 Claims, 3 Drawing Sheets

METHOD OF COMPENSATING FOR IMAGE FAULTS IN AN X-RAY IMAGE RECORDING

CROSS REFERENCE TO RELATED APPLICATIONS

This application claims priority to the German application No. 10 2004 027 163.1, filed Jun. 3, 2004 which is incorporated by reference herein in its entirety.

FIELD OF INVENTION

The invention relates to a method of compensating for image faults in a digital x-ray image recording which has been created by a radiographic source, an anti-scatter grid and a digital x-ray detector such as an image amplifier or solid-state image detector, said image faults having been caused by decentering, defocusing or defects of the anti-scatter grid or by the Heel effect and causing a reduction in the intensity of the primary radiation falling on the x-ray detector.

BACKGROUND OF INVENTION

Anti-scatter grids are used in x-ray systems so that when an object under examination is illuminated with x-rays only direct information-bearing primary radiation reaches the detector from the x-ray tube. The scattered radiation which makes the image noisy is blocked by the anti-scatter grid in order to improve the quality of the x-ray image. Anti-scatter grids consist of very thin strips of lead which are embedded into paper, with up to 80 strips per centimeter being used.

These lead strips of the anti-scatter grid are not arranged in parallel but are turned at a slight angle to each other and aligned to a specific optimum focal distance between the x-ray tube and the detector, for example 1500 mm. In practice however x-ray systems are operated at different tube-detector distances so that they are defocused, producing shadowing in the edge area of the x-ray image recording. Shadowing can also arise because the tube is not centered, that is it is not located precisely over the center point of the anti-scatter grid. Heel effect refers to the reduction in the intensity of rays on the anode side through the x-ray tube itself. Shadowing can also occur because of an incorrectly positioned or defective grid. This shadowing normally increases towards the edge at right angles to the direction of the lead laminations, while remaining constant in the direction of the lead laminations.

SUMMARY OF INVENTION

The problem here is that the reduction in intensity at the edge of the x-ray image may not amount to more than 40%, defined by the ICE (Convention 606271978). This means that the allowable distance range between the tubes and the detector in which the system may be operated is limited. Furthermore the shadows themselves then disturb the image when the system is operated in the valid range. In addition the shadowing can make diagnosis of the illness images more difficult.

It has already been proposed that these intensity reductions be corrected by a theoretical model. The Boldingh formula describes the intensity reduction as a function of specific characteristic grid values, for example the aspect ratio r, as well as the distance between the x-ray tube and the detector and the decentering. It has been shown however that this model can only reproduce the intensity reduction behavior of anti-scatter grids imprecisely. The deviations arising when the formula is applied are attributed to the fact that unknown variables such as incorrect grid positioning, grid defects or the Heel effect cannot be taken into account by Boldingh's formula.

An object of the invention is to specify a method which has a greater degree of accuracy when compensating for the image faults described above in an x-ray image recording.

This object is achieved by the claims.

Unlike the known method which is based on the Boldingh formula, the correction of the x-ray image recording is not undertaken solely on the basis of a theoretical model but the actual individual intensity reduction profile of the anti-scatter grid in the illumination system operated is determined in order to correct the x-ray image recording correspondingly. The advantage exhibited by the method in accordance with the invention is that all influencing factors which influence the x-ray image recording can be taken into account. The method can also be executed if the individual influencing factors and their effect on the x-ray image recording are not known in detail. With the method in accordance with the invention there is provision for the actual intensity reduction to be measured into which all influencing factors are entered. In this way unknown parameters, for example an incorrect positioning of the anti-scatter grid or asymmetrical effects such as the Heel effect of decentering can be recorded and corrected. The "data driven" model in accordance with the invention thus reflects the actual circumstances significantly more accurately than a theoretical model.

In a further embodiment of the invention provision can be made for blank images, in which there is no object between the radiographic source and the anti-scatter screen, to be recorded to measure the intensity reduction. These blank images are used to record the intensity reduction behavior of the entire x-ray system, consisting of radiographic source, anti-scatter screen and solid-sate image detector. The individual intensity reduction behavior can be determined on the basis of the blank images, furthermore the required correction parameters can be determined with which the x-ray image recording can subsequently be corrected. The production of the blank image is thus a type of calibration measurement.

With the method it is especially preferred for the x-ray image to be recorded as a digital image matrix with columns and rows and for a profile line describing the intensity reduction to be calculated. The x-ray image recording delivers as a result a matrix with individual values for each x-ray sensitive pixel of the x-ray detector, for example of a solid-state image detector. In this case for example low pixel values of the digital image can represent high x-ray incidence and vice versa. The blank images recorded of anti-scatter grids show that the intensity reduction of the primary radiation increases from the middle of the anti-scatter grid over which the x-ray source is located towards the sides. In the direction at right angles to this of the plane of the anti-scatter grid in parallel to the direction of the lead laminations, represented by the columns of the image, the intensity reduction can be assumed to be constant in a initial approximation. Accordingly a profile line describing the intensity reduction which is representative for the anti-scatter grid and for the entire x-ray system can be calculated from the image matrix which represents a surface profile of the intensity reduction.

The summed values of the individual columns which form a one-dimensional vector can be smoothed by multiple lowpass filtering. In this way individual extreme values can be filtered out.

With the method it is further preferred that the profile line embodied as a vector is scaled to values between 0 and 1. For scaling the vector is divided by its maximum value.

In a further embodiment of the invention there can be provision for the minimum of the profile line to be determined. This minimum which lies in the vicinity of the center of the anti-scatter grid is the location with maximum transmission. However it does not necessarily have to lie exactly in the center but can for example be shifted by a decentering of the tubes or by the Heel effect.

With the method accordance with the invention there can be provision that for the sections of the profile line to the left and the right of the minimum the equations of a straight line of the best fitting lines of the corresponding parts of the profile line are determined. To obtain a uniform description of the profile the average values of the gradients and the axis sections of the two individual straight lines are determined. Thus the two areas to the right and the left of the center can be approximated by a single best fitting line.

With the method in accordance with the invention there can further be provision for the x-ray image recording to be corrected with reference to the minimum of the profile line and the gradient of the equations of a straight line. The minimum and the gradients determined serve as correction parameters for the intensities of the x-ray image recording. The decentering, meaning the shifting of the x-ray emitter center point is already known. Likewise the gradient of the straight lines is known. The individual columns of the image matrix are multiplied by these correction parameters so that corrected recorded images are produced which no longer show any intensity decrease effects. The image brightness can be corrected on the basis of the correction parameters.

In accordance with the invention there can also be provision for a number of blank images to be recorded at different focal distances between the radiographic source and the solid-state image detector and/or various decenterings to be recorded in order to determine the relationship between the distance between radiographic source and solid state image detector as well as the decentering and the straight line parameters including the profile minimum if this relationship is known, the best fitting lines can subsequently be determined for any given distance between the radiographic source and the detector.

The invention also relates to an x-ray system for recording x-ray images, comprising a radiographic source, an anti-scatter grid and an x-ray detector. In accordance with the invention the x-ray system is embodied to compensate for image faults by means of the method described.

BRIEF DESCRIPTION OF THE DRAWINGS

Further advantages and details of the invention will be explained on the basis of an exemplary embodiment with reference to the Figures. The Figures are schematic diagrams and show.

DETAILED DESCRIPTION OF INVENTION

Figure 1:
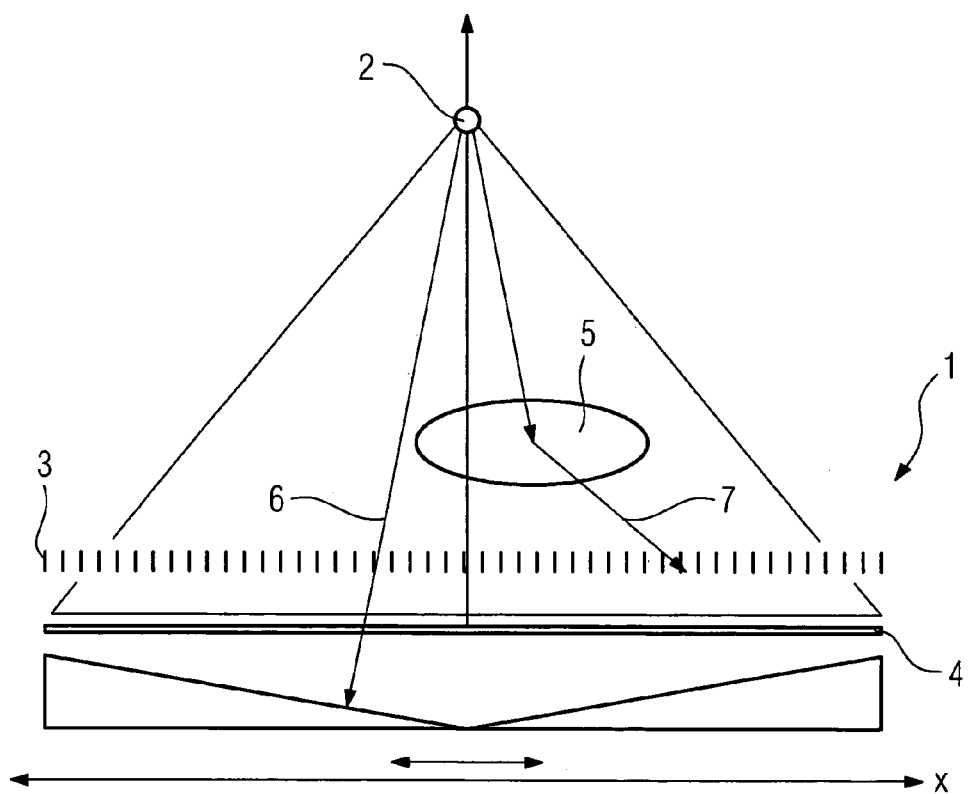
FIG. 1 an x-ray system in accordance with the invention.

The x-ray system 1 shown in FIG. 1 consists of a schematic diagram of an x-ray tube 2, an anti-scatter grid 3 and an image detector 4 arranged below the anti-scatter grid. On illumination of an object 5, which is located between the x-ray tube 2 and the anti-scatter grid 3, direct information-bearing primary radiation 6 passes through the object 5 to reach the detector 4. A part of the radiation however is deflected by inhomogeneities, for example bones, in the object and thus becomes scattered radiation which disturbs the image. This is subsequently blocked off by the lead laminations of the anti-scatter grid 3. In this way scattered radiation 7 which disturbs the image is prevented from reaching the detector 4.

With the x-ray system 1 the x-ray tube 2 is adjustable vertically so that different distances between the x-ray tube 2 and the detector 4 can be set. Since the individual lead strips from which the anti-scatter grid is constructed are inclined at a slight angle, the anti-scatter grid 3 is only optimally aligned to the x-ray tube 2 at a specific focal length, which is 1500 mm in the exemplary embodiment shown. If the x-ray system is operated with a different distance between the x-ray tube 2 and the detector 4 so that it is defocused, shadowing occurs in the edge area with conventional image recording methods.

Figure 2:
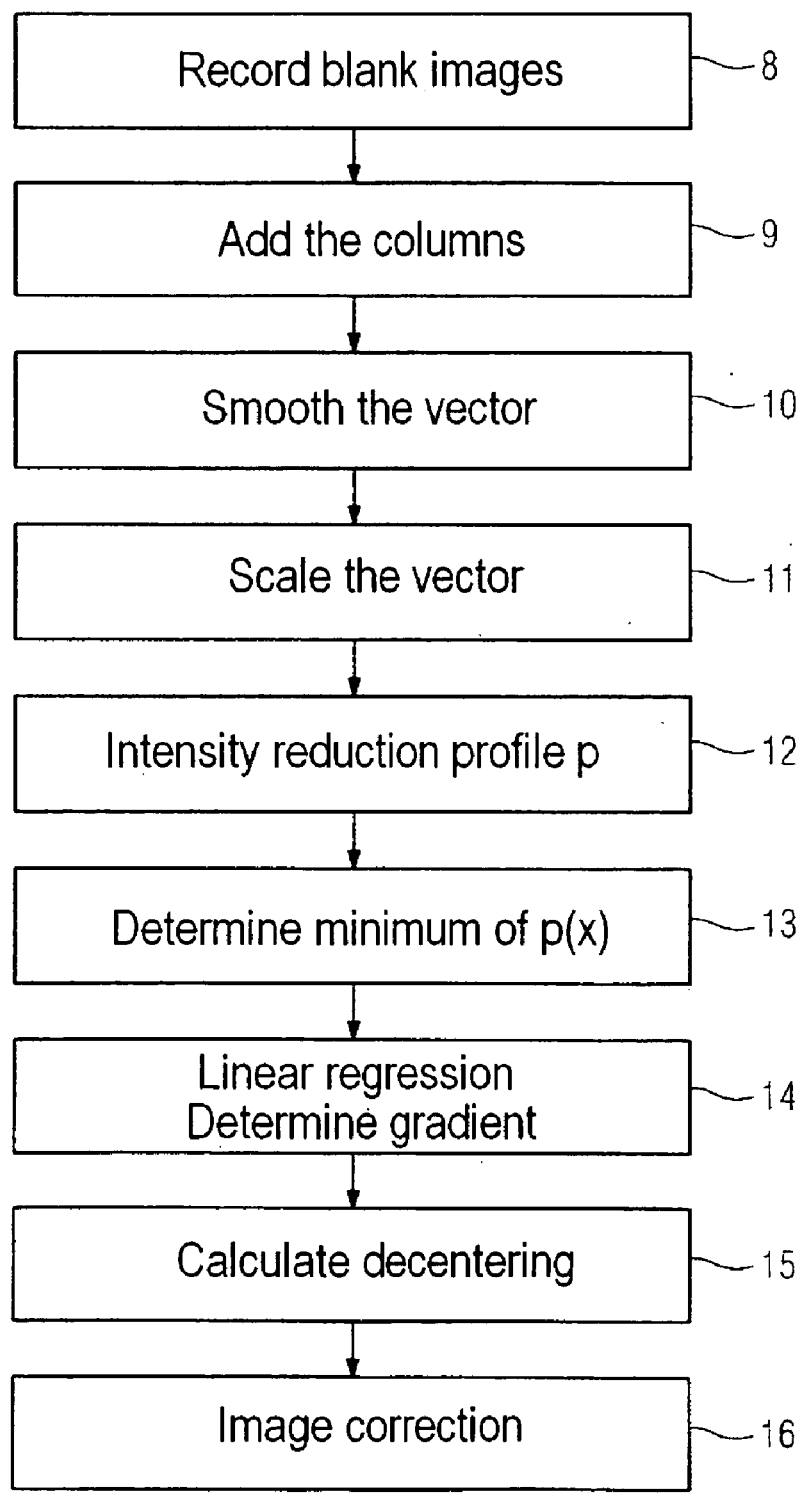
FIG. 2 a flowchart of the method in accordance with the invention.

FIG. 2 shows a flowchart of the method in accordance with the invention.

The method for correction of image faults is based on calculating the intensity reduction profile of the anti-scatter grid 3. To this end different blank images are included in step 8. To record a blank image there is no object between the x-ray tube 2 and the anti-scatter grid 3. The blank images thus reflect the intensity reduction of the radiation by the anti-scatter grid 3. For a specific distance between the x-ray tube 2 and the anti-scatter grid 3 or the detector 4 it is sufficient to record one blank image. The method however provides for a number of blank images to be produced at different focal lengths f and/or for different sideways deflections of the tube (defocusing) so that it is possible to correct all x-ray images, regardless of the relevant focal distance.

The computation of the intensity reduction profile for the fixed focal distance f will be explained below. The digital image is available as a matrix with x columns and y rows of intensity values m(ij).

The equation below sums the columns of the image matrix vertically and a one-dimensional vector is obtained which is smoothed by multiple lowpass filtering (steps 9, 10):

$$I(x) = \sum_{i=1}^{Y_p} m_{ix} \quad (1)$$

In procedural step 11 the vector is scaled, so that all values lie between 0 and 1. These values correspond to the percentage intensity reduction. It is assumed here that the intensity reduction is 0% in the center and 100% at the shielded edges. The intensity reduction profile is as follows:

$$p(x) = 1 - \frac{I(x)}{\max(I(x))} \quad (2)$$

The scaling of the vector is shown in the flowchart of FIG. 2 as procedural step 11. The resulting intensity reduction profile is at its minimum in the vicinity of the center of the anti-scatter grid 3, which can be determined in procedural step 13 by the following equation:

$$x_m := ARGMIN(p(x)) \quad (3)$$

In procedural step 14 the intensity reduction profile is divided up into a left-hand part and a right-hand part and a linear regression of both parts is computed, then the corresponding parameters of the two individual equations are averaged. In this way the intensity reduction profile can be expressed by a straight line equation. The equation of the profile line is:

$$V(x) = M \cdot |x - x_m| + B_d \quad (4)$$

In this equation M is the gradient of the linear intensity reduction profile.

With the Boldingh formula the expected intensity reduction of the radiation can be calculated as a function of the distance f between the X-ray tube and the detector for a known decentering (shift) z for each point c:

$$V(c) = \begin{cases} r\left(\frac{c+z}{f} - \frac{c}{f_0}\right) & \text{if } \{ f \leq f_0 \\ r\left(\frac{c}{f_0} - \frac{c+z}{f}\right) & \text{if } \{ f > f_0 \end{cases} \quad (5)$$

By transformation the following equation is obtained:

$$V(x) = F \cdot \left|\frac{r}{f} - \frac{r}{f_0}\right| \cdot |x - x_m| \quad (6)$$

In FIG. 1 the intensity reduction profile V(x) is shown below the detector 4 in qualitative terms.

With r being a characteristic value of the anti-scatter grid, known as the shaft ratio which describes height to width of the paper strip.

The factor $$F := \frac{mm}{Pixel} \quad (7)$$

is a variable which allows the formula to be used on pixels instead of on "millimeters". This value is the opposite value of the pixel density. With equation (6) and equation (3) the decentering in millimeters can be defined (procedural step 15):

$$z(x_m) = F \cdot (x_m - Xc) \cdot |1 - f/f_o| \quad (8)$$

The main factor here is that it is of no significance how the shift is triggered. Since the computation method starts from the actual intensity reduction method, both the influences of the Heel effect and also the decentering of the x-ray tube 2 or other influences can be taken into account.

After the variables $x_m$ and M have been determined the image can be corrected in procedural step 16 by multiplying each column by the correction factor:

$$C(x) = \frac{1}{1 - M \cdot |x - x_m|} \quad (9)$$

This formula can be used to correct the image brightness.

A description is given below of how the intensity reduction profile can be computed for any given distances between the X-ray tube and the detector. So that different focal distances f can be taken into account for image correction, a series of calibration images are recorded for different states f, then the required correction parameters are calculated.

To calculate the decentering $x_m$ for any given focal distances f, a number of blank images are recorded with an anti-scatter grid and $x_m$ and z are determined. The images can be recorded with different radiation doses. It has been discovered that a linear relationship exists between the decentering and the distance f between the x-ray tube and the image detector. On the basis of the blank images for the calibration the decentering z(f) is determined for each blank image as well as subsequently the linear adaptation of the decentering defined over the distance f. With this linear adaptation the decentering $x_m$ can now be determined for any given distance f, i.e. between the calibration points.

To enable the image to be corrected the gradient of the intensity reduction profile for given distances f must also be calculated. There are two possible options for calculating the profile gradient.

The first variant is based on the Boldingh formula and calibration is with reference to the measurement data. Calibration consists of calculating the linear relationship $$M_B \approx K \cdot M_D \quad (10)$$

with $M_D$ being the gradient of the measurement data. K is a calibration factor and specifies the relationship between the profile calculated from the measured data and the Boldingh formula. In this case the peripheral condition that $M_D=0$ for $f=f_0$ should apply is to be taken into account. For any given distances f the intensity reduction profile is calculated by first determining the decentering. Subsequently the intensity reduction is calculated using the Boldingh formula and multiplied by K. This produces the intensity reduction profile for the relevant focal distance f. The radiological image is then corrected with equation (9).

With the second variant the Boldingh formula is not used, but the model is based entirely on the measured data. From the different calibration images the gradients for the right and left half $M_R$ and $M_L$ are calculated by a linear approximation separately for $f<f_0$ and $f>f_0$. If the x-ray tube is at its optimum focus the peripheral condition $M_R(f_0)=M_L(f_0)=0$ applies, meaning that no correction is necessary. For a given distance f the intensity reduction profile is determined by calculating the decentering. Subsequently the gradient of the intensity reduction profile is calculated from the linear approximation of the calibration images. This produces the intensity reduction profile for this focal distance f. The radiological image can again be corrected with equation (9).

Figure 3A:
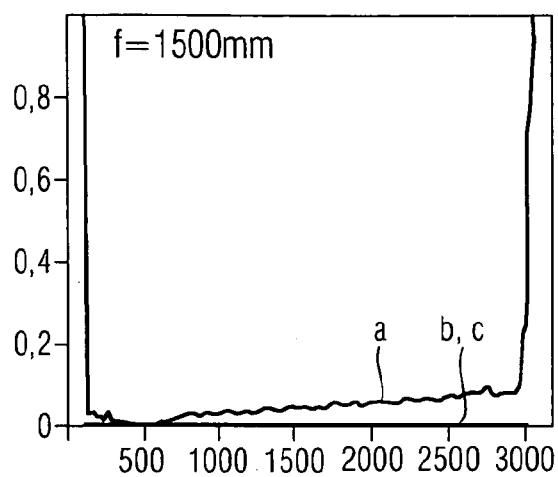
FIG. 3a to 3c diagrams with measured and computed intensity reduction profiles for different distances between radiographic source and detector.
Figure 3B:
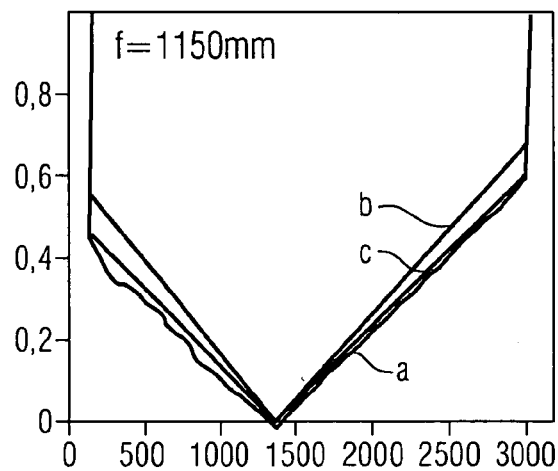
Figure 3C:
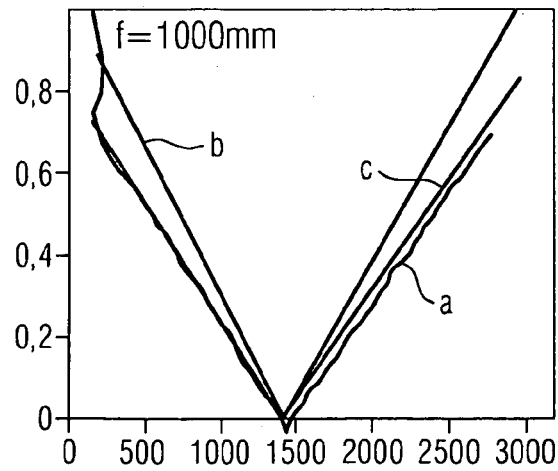

FIGS. 3a to 3c show the measured and calculated intensity reduction profile for different distances between the x-ray tube and the detector. The horizontal axis corresponds to the x-axis shown in FIG. 1. The intensity reduction is entered on the vertical axis, and this can be between 0 and 1. Three curves are also shown in each of FIGS. 3a to 3c. Curve a represents the smoothed profile (Ix). Curve b represents the intensity reduction according to the Boldingh formula. Curve c shows the intensity reduction calculated in accordance with the inventive method.

In FIG. 3a the focal distance is f=1500 mm. It can be seen that the differences are comparatively small between profile of curve a based on the measured values and the curves b and c.

FIG. 3b represents the case in which the focal distance amounts to f=1150 mm. It can be seen that curve c delivers a significantly better approximation of the intensity reduction than does the Boldingh formula (curve b).

The same applies to the focal distance f=1000 mm shown in FIG. 3c. The differences between curves a and c only amount to a few percent.

Since the anti-scatter grids are currently constructed from lead strips and the intensity reduction is thus constant in one direction, the direction of the lead laminations, the one-dimensional correction in the direction of the columns is sufficient. The method can however usefully be expanded to two dimensions if another scanning method, for example a grid, requires this.

The invention claimed is:

1. A method of compensating for image faults in a digital x-ray image recorded by an x-ray system having a radiographic source, an anti-scatter grid and a digital x-ray detector, wherein the image faults result from de-centering, defocusing or defects in the anti-scatter grid or from the Heel effect, the image faults leading to an intensity reduction of primary radiation falling on the x-ray detector, the method comprising:
   determining a first intensity of the primary radiation before the primary radiation hits the anti-scatter grid;
   determining a second intensity of the primary radiation after the primary radiation has hit the anti-scatter grid;
   determining a reduction in intensity of the primary radiation caused by the anti-scatter grid based on the first and second intensities;
   determining a set of correcting parameters based on the determined reduction in intensity of the primary radiation; and
   correcting the x-ray image using the set of correcting parameters.

2. The method according to claim 1, wherein the digital x-ray detector is an image amplifier or a solid-state image detector.

3. The method in accordance with claim 1, wherein determining the first intensity of the primary radiation includes recording blank images with no object present in a radiation path between the radiographic source and the anti-scatter grid.

4. The method in accordance with claim 3, wherein a plurality of blank images corresponding to different distances between the radiographic source and the x-ray detector are recorded for determining a function related to intensity-reducing results caused by a de-centering of the anti-scatter grid depending on the different distances.

5. The method in accordance with claim 1, wherein
   the x-ray image is recorded as a digital image matrix having a plurality of columns and rows, and
   determining the reduction in intensity of the primary radiation includes calculating a profile line representing the reduction in intensity reduction.

6. The method according to claim 5, wherein calculating the profile line includes summing up the columns.

7. The Method in accordance with claim 6, wherein the profile line is a one-dimensional vector having the summed columns as its vector elements.

8. The method in accordance with claim 5, wherein the profile line is smoothed by repeatedly applying a low-pass filter algorithm to the profile line.

9. The method in accordance with claim 5, wherein the profile line is a vector having vector elements scaled to values between 0 and 1.

10. The method in accordance with claim 5, wherein a center of the reduction in intensity is determined by locating a minimum of the profile line.

11. The method in accordance with claim 10, wherein a first and a second linear equation are determined, the first linear equation representing a left part of the profile line relative to the located minimum, and the second linear equation representing a right part of the profile line relative to the located minimum.

12. The method according to claim 11, wherein the first and second equations are determined using a linear regression algorithm.

13. The method in accordance with claim 12, wherein the set of correcting parameters includes the minimum of the profile line and a gradient of the first and second equations.

14. The method in accordance with claim 13, wherein an image brightness of the x-ray image is corrected using the minimum of the profile line and the gradient of the first and second equations.

15. An x-ray system for recording an x-ray image, comprising:
   a radiographic source;
   an anti-scatter grid;
   an x-ray detector; and
   a processing device for compensating for image faults resulting from de-centering, defocusing or defects in the anti-scatter grid or from the Heel effect, the image faults leading to an intensity reduction of primary radiation falling on the x-ray detector, wherein the processing device is configured to:
   determine a first intensity of the primary radiation before the primary radiation hits the anti-scatter grid;
   determine a second intensity of the primary radiation after the primary radiation has hit the anti-scatter grid;
   determine a reduction in intensity of the primary radiation caused by the anti-scatter grid based on the first and second intensities;
   determine a set of correcting parameters based on the determined reduction in intensity of the primary radiation; and
   correct the x-ray image using the set of correcting parameters.

* * * * *